United States Patent [19]

Rauscher

[11] 4,198,626
[45] Apr. 15, 1980

[54] INTRAVENOUS ALARM DEVICE

[76] Inventor: Frank J. Rauscher, 4908 Mt. View Ave., San Bernardino, Calif. 92407

[21] Appl. No.: 830,093

[22] Filed: Sep. 2, 1977

[51] Int. Cl.² ............................................. G08B 21/00
[52] U.S. Cl. ................................ 340/613; 128/214 E; 177/48; 177/251; 222/39; 340/384 E
[58] Field of Search .................... 340/613, 625, 384 E; 177/45, 46, 47, 48, 67, 251; 128/214 C, 214 E, DIG. 13; 222/39, 47, 49, 58

[56] References Cited

U.S. PATENT DOCUMENTS

| 1,511,404 | 10/1924 | Fiedler | 177/251 X |
| 2,160,276 | 5/1939 | McKee | 340/613 X |
| 3,759,337 | 9/1973 | Luedke et al. | 177/251 X |
| 3,885,639 | 5/1975 | McLarrin | 177/251 X |
| 3,922,672 | 11/1975 | Birt et al. | 340/384 E |
| 3,977,567 | 8/1976 | Rudd | 222/39 |
| 4,095,658 | 6/1978 | Kendall et al. | 128/214 E X |

FOREIGN PATENT DOCUMENTS 2334568  1/1974  Fed. Rep. of Germany ....... 128/214 E Primary Examiner—John W. Caldwell, Sr.
Assistant Examiner—Daniel Myer
Attorney, Agent, or Firm—Christie, Parker & Hale

[57] ABSTRACT

An intravenous alarm device provides an alarm signal to indicate that a predetermined amount of liquid remains in a liquid dispensing container of the type such as an I.V. bottle or bag adapted to be suspended from an arm. The device includes an attitude-sensitive transducer such as a mercury switch defining a reference axis, and the alarm signal is given when the reference axis extends along a line in predetermined angular relationship with the horizontal. The device further includes a structure supporting the transducer, with the structure including, at a first point thereof, a hanger portion to suspend the device from such an arm; at a second point thereof, a holding portion to suspend the container from the device; and, at a third point thereof, a device center of gravity. The first, second, and third points are spaced to define vertices of a triangle. In use, the structure orients the reference axis at an angle relative to the horizontal with the instantaneous angle being dependent upon the weight of the liquid remaining in the suspended liquid container.

5 Claims, 3 Drawing Figures

INTRAVENOUS ALARM DEVICE

BACKGROUND OF THE INVENTION

In general, this invention relates to alarm-signaling devices of the type used to warn hospital attendants that only a predetermined amount of liquid remains in a container dispensing liquid intravenously into a patient. More particularly, it relates to such a device in which an attitude-sensitive transducer initiates the giving of an alarm signal.

It has long been recognized that there exists a need for a device to provide an alarm signal to alert hospital attendants that only a predetermined amount of liquid remains in a container dispensing liquid intravenously to a patient. Various patents each give a comprehensive explanation of the reasons why this need exists; see, for examples, U.S. Pat. No. 3,942,526 and U.S. Pat. No. 3,977,567.

In one class of known I.V. alarm devices, there is used a relatively simple arrangement wherein a spring suspends the liquid container. The biasing force of the spring causes the container to rise as liquid is dispensed, and an electrical switch is activated when the container reaches a predetermined position. Although simple in construction, the devices in this class are cumbersome and unreliable.

Other proposed devices suffer from the disadvantage of complexity of construction and attendant expense.

With reference to U.S. Pat. No. 3,977,567, the device disclosed therein incorporates a moving member, viz, a balance arm, that rotates rather than translating up and down as do the devices of spring supporting class. Similar to those devices, the balance arm has a portion that acts like a switch contact for initiating an alarm signal when that portion is rotated into alignment with a fork-shaped support member. At the lower end of the balance arm there are positioned along a straight line various holes including a hole for receiving a pin pivoting the balance arm to the support member. The other holes are used for holding the container and counterweights. To use this device, it is necessary to perform a number of manipulative steps defining a pre-balancing procedure. In this procedure, first, the balance arm is oriented in a predetermined, balanced relationship with respect to the support member by appropriately positioning a counterweight, and, then, the counterweight is moved to a different position thereby causing the balance arm to become unbalanced and swing until a stop member limits its angular movement. Following this procedure, liquid is dispensed from the container and the combined weight of bottle and liquid decreases. Eventually, a point is reached where a torque is imposed on the balance arm in a direction causing it to rotate back toward the pre-balance position. Another factor, apart from the above-described time-consuming pre-balancing procedure, bearing mention in a description of this patented device is that, as disclosed in the patent, it is intended for use with two of the standard sized bottles, viz, 500 cc and 1000 cc bottles. There is no disclosure as to use with the newer, much lighter plastic bags. Moreover, the ratio of the weights involved here is substantial, thereby rendering it difficult to adapt this device to handle such bags. In particular, an empty plastic I.V. bag typically weighs only 40 grams, plus or minus 4 grams. On the other hand, an empty standard 1000 cc bottle weighs 530 grams, plus or minus 21 grams.

SUMMARY OF THE INVENTION

An intravenous alarm device in accordance with this invention provides an alarm signal to indicate that a predetermined amount of liquid remains in a liquid dispensing container of the type adapted to be suspended from an arm.

The device comprises attitude-sensitive transducer means, preferably including a mercury switch, defining a reference axis. The transducer means includes means for producing such an alarm signal when the reference axis extends along a line in predetermined angular relationship with the horizontal. The device further comprises a structure including means supporting the attitude-sensitive means.

The structure has at a first point thereof a hanger portion to provide for suspending the device from such an arm. The hanger portion defines an axis of revolution perpendicular to the above-mentioned line along which the reference axis extends when the alarm signal is produced. The structure has at a second point thereof a holding portion from which such a liquid dispensing container can be suspended. It has defined at a third point thereof a device center of gravity. Significantly, the first, second, and third points are spaced relative to each other to define vertices of a triangle. Owing to this significant feature, the structure, while being suspended from such an arm and having suspended from it such a liquid dispensing container, orients the reference axis at a time-varying angle relative to the horizontal with the instantaneous magnitude of the time-varying angle being dependent upon the weight of the liquid remaining in the suspended liquid container.

Preferably, the device further includes a counterweight and means for securing the counterweight to the structure at any one of a plurality of points thereby to shift the structure center of gravity to a point suitable for the type of container being used in conjunction with the device. An advantage of the device is its adaptability for use with any one of the standard sized bottles or lighter plastic I.V. bags.

Other advantageous features recited in claims made herein will be better appreciated upon consideration of the ensuing detailed description of the presently preferred embodiment.

DETAILED DESCRIPTION

Figure 1:
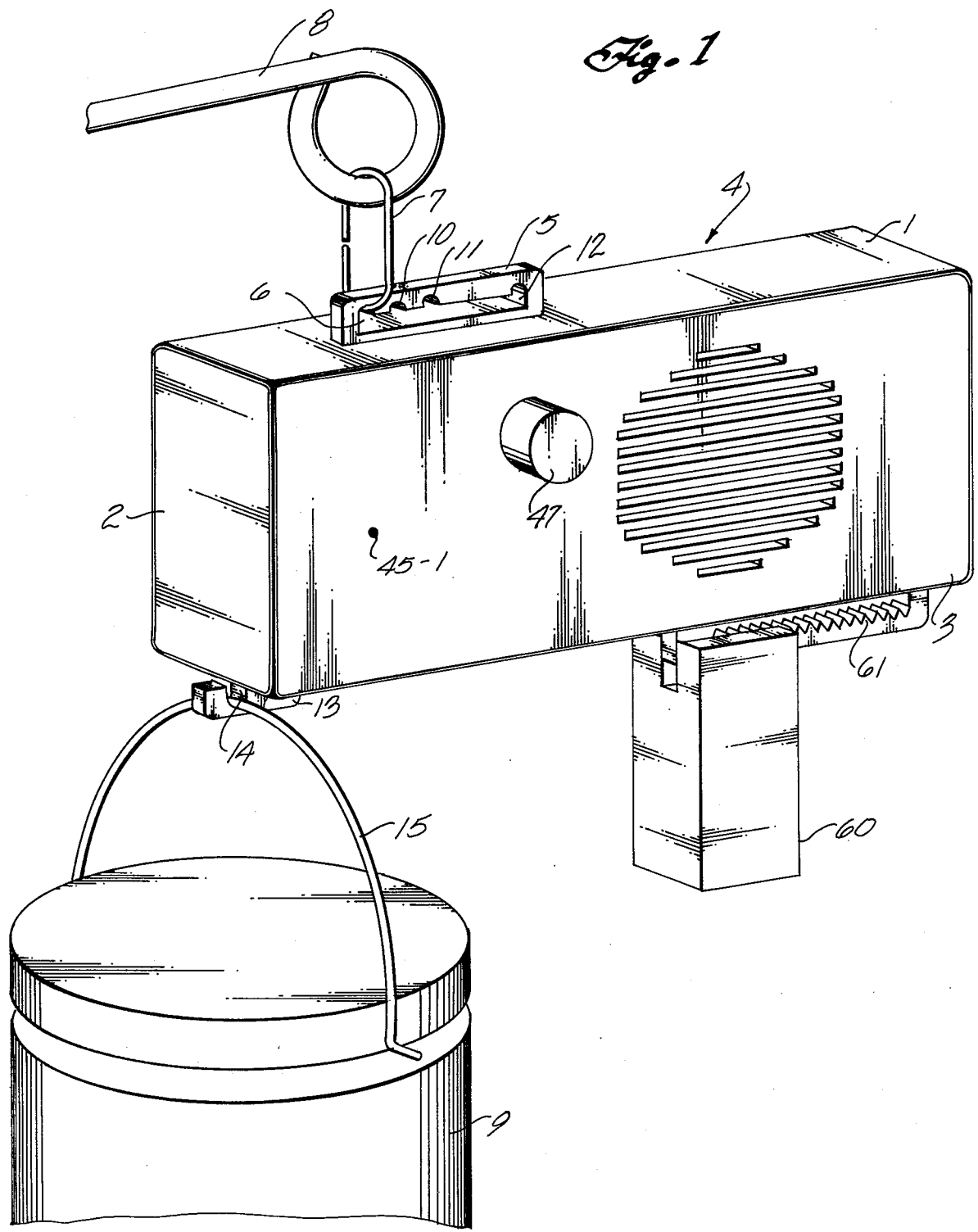
FIG. 1 is a perspective view of a device embodying the present invention.

In FIG. 1, a device embodying this invention is shown in perspective illustrating top, left side, and front walls 1, 2, and 3 of an elongated casing 4.

A hanger portion 5 of casing 4 projects upwardly from top wall 1. A series of spaced-apart grooves including groove 6 are formed in hanger portion 5 with each groove extending in a direction parallel to the side walls of casing 4. A hook 7 is provided for suspending casing 4 from an external cantilevered arm 8. Only a portion of arm 8 is shown; the remaining portion thereof provides for a supporting connection to the head of a bed, rack, or the like. When the device is used in conjunction with a standard 1000 cc bottle such as bottle 9, hook 7 is placed in groove 6 which is the nearest of the grooves to left side wall 2. When the device is used in conjunction with a standard 500 cc bottle (not shown), hook 7 is placed in the adjacent groove 10. Two other grooves, viz., grooves 11 and 12, are provided for use in conjunction with a standard 250 cc bottle and a plastic bag respectively.

A holding portion 13 of casing 4 has a groove 14 serving as a seat for handle 15 of bottle 9.

Figure 2:
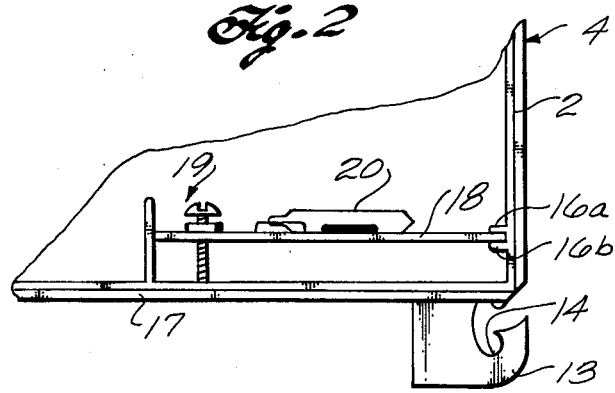
FIG. 2 is an elevation view of an interior portion of the device of FIG. 1 in which there is shown an arrangement for supporting a transducer element of the device.

As shown in FIG. 2, a pair of vertically spaced-apart flanges 16a and 16b project inwardly within casing 4 from left side wall 2. Flanges 16a and 16b extend parallel to bottom wall 17 of casing 4. One end of a circuit board 18 is secured between flanges 16a and 16b. The opposite end of circuit board 18 is adjustably spaced above bottom wall 17 by a set screw arrangement 19.

A conventional elongated two-contact mercury switch 20 is supported on circuit board 18. A mercury switch suitable for use in an embodiment of this invention is sold by MICRO SWITCH, a division of Honeywell, under the designation X66470-mer. Mercury switch 20 defines a reference axis. Depending upon the orientation of the reference axis relative to the horizontal, the mercury within switch 20 is positioned either away from contacts 21 and 22 (FIG. 3) or in connection with them. Commercially available mercury switches are characterized by an angle relative to horizontal at which the switch closes. Such switches are also characterized by a minor degree of hysteresis and accordingly separate specifications are applicable as to "make" and "break." Preferably, a mercury switch used in this device is such that the difference between its make and break angles is approximately 0.7 degrees. By adjusting set screw arrangement 19 to tilt board 18 in one direction or the other relative to bottom wall 17, a compensation can easily be achieved such that the make occurs whenever casing 4 is oriented such that bottom wall 17 is within 0.2 degrees of horizontal.

In use of the device, the make occurs when a predetermined amount of liquid remains in the suspended container, and, in response, an alarm is given. Preferably, an audible alarm signal is produced.

Figure 3:
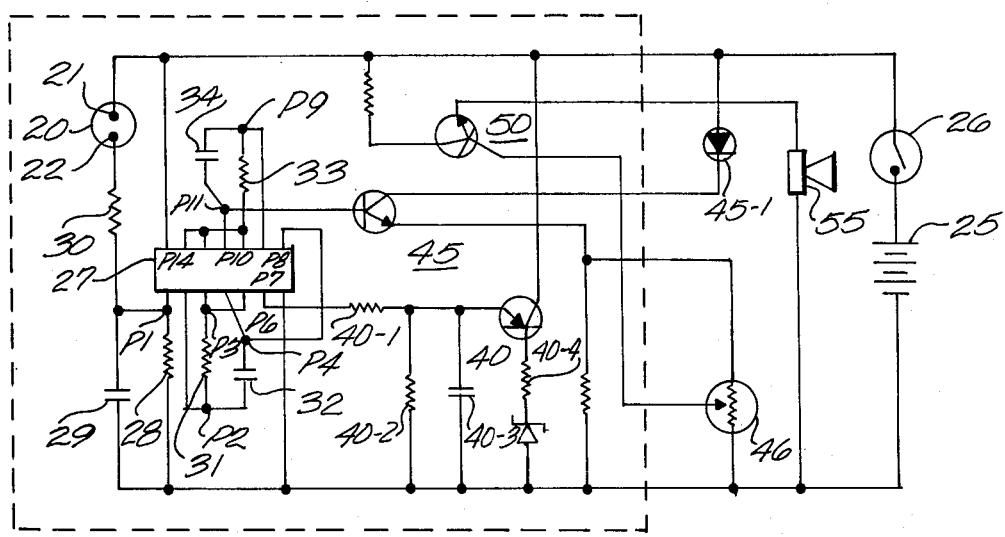
FIG. 3 is a block and schematic drawing of circuitry involved in producing an alarm signal.

With reference to FIG. 3, there will now be described circuitry used in the preferred embodiment to produce such an audible alarm.

A battery 25, preferably a small nine-volt battery, provides operating power to the remaining circuitry of FIG. 3 when on ON/OFF switch 26 is closed to activate the device. A conventional quad NAND gate integrated circuit 27 is included in the circuitry. A suitable such integrated circuit is available from a number of semiconductor manufacturers under the designation CD4011. The four individual two-input NAND gates within circuit 27 are not separately shown. Pin P14 of circuit 27 is its $V_{cc}$ terminal and thus is connected to switch 26 to receive positive voltage. Pin P7 of circuit 27 is its ground terminal and thus is connected to the negative terminal of battery 25.

The first NAND gate has one of its inputs (P1) connected to the junction of a resistor 28, a capacitor 29, and a resistor 30. The output (P3) of the first NAND gate is fed back to its other input (P2) through a resistor 31. The second NAND gate has one of its inputs connected to the output of the first NAND gate and its output (P4) is fed back through a capacitor 32 to P2. The first two NAND gates, connected as described with resistor 31 and capacitor 32, form a gated oscillator that oscillates while a '1' level (i.e., a relatively high positive voltage) is presented to pins P1 and P6. Resistors 28 and 30 and capacitor 29, connected as described, form a delay circuit for ensuring that the audible alarm will not inadvertently be given.

The third NAND gate has one of its inputs (P8) connected to the output P4 of the second NAND gate. The output (P10) of the third NAND gate is fed back to its other input (P9) through a resistor 33. The fourth NAND gate has its two inputs connected together so that it defines a simple inverter, and its output (P11) is fed back through a capacitor 34 to P9. The third and fourth NAND gates, connected as described with resistor 33 and capacitor 34, form a modulated oscillator. The modulation is such that tone bursts are produced as the audible signal.

A threshold-determining circuit is generally indicated at 40. A pnp transistor is used in circuit 40 and is connected in the conventional inverted connection whereby its current gain is substantially reduced. So long as battery 25 is sufficiently charged that its output voltage exceeds a threshold of approximately 6.2 volts, the inverted-connected transistor conducts and the components connected to its emitter smooth the voltage presented to pin P6. When battery 25 discharges from prolonged use to the point at which its output drops below the threshold, the inverted connected transistor turns off. This causes the voltage presented to pin P6 to drop to such a low voltage as to cause the modulated oscillator to produce a continuous oscillation. It will be appreciated that this feature is advantageous in that immediate warning is given by a continuous audible tone that the battery voltage is low and that a new battery should be installed. An emitter follower circuit generally indicated at 45 couples the output of the gated oscillator to a potentiometer 46. An LED 45-1 is connected to the collector of the npn transistor in circuit 45 to provide for giving a visual alarm. A knob 47 (FIG. 1) is provided to adjust potentiometer 46 such that the audible alarm is produced at a desired level. Another emitter follower circuit generally indicated at 50 couples the output of potentiometer 46 to a speaker 55.

Suitable values for the aforegoing components are as follows: Resistor 30, 8.6 Meg.; Resistor 28, 20 Meg.; Resistor 31, 4.7 Meg.; Resistor 33, 100 K; Resistor 40-1, 4.7 Meg.; Resistor 40-2, 100 K; Resistor 40-4, 33 K; Capacitor 29, 0.1 µf; Capacitor 32, 0.1 µf; Capacitor 34, 0.01 µf, and Capacitor 40-3, 0.01 µf. Suitable transistors are 2N697 for the npn transistors and SK3114 for the pnp transistor.

A particularly significant feature of the invention will now be described with reference to FIG. 1. Casing 4 together with the components housed in it and with a counterweight 60 defines a device center of gravity. The location of the center of gravity can be adjusted by moving counterweight 60 from notch to notch along a track 61 from which the counterweight is suspended. In a specific embodiment, the combined mass of casing 4, its internal components, and counterweight 60 is 329 grams. With the counterweight occupying the center notch, the device center of gravity is located at a point 3.125 inches to the right of groove 14 and 0.844 inches higher than groove 14. It will be appreciated that three points, viz, the point at which the center of gravity is located, the point from which the liquid container is suspended, and the point from which casing 4 is suspended, define vertices of a triangle. Owing to this feature, casing 4 causes, while liquid is being dispensed, the reference axis of switch 20 to be oriented at a time-varying angle relative to the horizontal with the instantaneous magnitude of the time-varying angle being dependent upon the weight of the liquid remaining in the suspended liquid container. Although a more detailed mathematical treatment of this matter is given below, a general understanding of this can be appreciated from the following point. In use, casing 4 revolves around an axis of revolution defined at the point where hook 7 is placed. A balanced or equilibrium condition involves having the counter-clockwise torque imposed thereon equal the clockwise torque imposed thereon. When viewed from the front, container 9 being to the left of the axis of revolution imposes a counter-clockwise torque whereas the device center of gravity, being to the right, imposes a clockwise torque. As liquid is dispensed, the weight of the suspended container decreases and casing 4 revolves in a clockwise direction. As a result, the moment arm factor of the counter-clockwise directed torque increases, and the moment arm factor of the clockwise directed torque decreases. Thus, there is a continuum of stable equilibrium angular positions.

There will now be set forth a more detailed mathematical analysis of this matter. The terms used in the following equations are:

(1) $\phi$ is the angle defined between the reference axis of switch 20 (FIG. 2) and the horizontal. $\phi$ is positive when the right side (i.e., the counterweight side) of casing 4 is higher than the left side.

(2) $\theta_g$ is the angle defined between the vertical and a line extending from the axis of revolution to the device center of gravity. $r_g$ is the length of this line.

(3) $\theta_d$ is the angle defined between the vertical and a line extending from the axis of revolution to groove 14 from which the liquid container hangs. $r_d$ is the length of this line.

(4) A point O' is defined at the intersection of a coordinate line parallel to the bottom wall of casing 4 and passing through the device center of gravity, and another line perpendicular to said coordinate line and passing through the axis of revolution. O'A is the distance between O' and the axis of revolution. O'E is the distance between O' and the device center of gravity.

(5) A point O" is defined at the intersection of the above-mentioned coordinate line that passes through the axis of revolution and a line perpendicular to said coordinate line and passing through groove 14.

(6) $MA_g$ and $MA_d$ are the moment arms.

(7) $W_g$ is the combined mass of casing 4, its internal components, and the counterweight. $W_d$ is the total mass of the suspended container. O"A is the distance between O" and the axis of revolution. O"F is the distance between O" and groove 14.

The following equations are self-explanatory.

$$\theta_g = \phi + \sin^{-1}(O'E/r_g) \qquad \text{Eq. 1}$$

$$\theta_d = \sin^{-1}(O''F/r_d) - \phi \qquad \text{Eq. 2}$$

$$MA_g = r_g \sin \theta_g \qquad \text{Eq. 3}$$

$$MA_d = r_d \sin \theta_d \qquad \text{Eq. 4}$$

$$(W_g)(MA_g) = (W_d)(MA_d) \qquad \text{Eq. 5a}$$

$$(W_g)(r_g)(\sin \theta_g) = (W_d)(r_d)(\sin \theta_d) \qquad \text{5b}$$

$$(W_g)(r_g)(\sin [\phi + \sin^{-1}(O'E/r_g)]) = (W_d)(r_d)(\sin [\sin^{-1}(O''F/r_d) - \phi]) \qquad \text{5c}$$

$$(W_g)(r_g)\{\sin \phi \cos [\sin^{-1}(O'E/r_g)] + \cos \phi \sin [\sin^{-1}(O'E/r_g)]\} = (W_d)(r_d)\{\sin [\sin^{-1}(O''F/r_d)] \cos \phi - \cos [\sin^{-1}(O''F/r_d)] \sin \phi\} \qquad \text{5d}$$

$$(W_g)(r_g)\{(\sin \phi)(O'A/r_g) + (\cos \phi)(O'E/r_g)\} = (W_d)(r_d)\{(O''F/r_d) \cos \phi - (O''A/r_d)(\sin \phi)\} \qquad \text{5e}$$

$$(W_g)/\cos \phi \{(\sin \phi)(O'A) + (\cos \phi)(O'E)\} = (W_d/\cos \phi)\{(O''F)(\cos \phi) - (O''A)(\sin \phi)\} \qquad \text{5f}$$

$$W_g\{(\tan \phi)(O'A) + O'E\} = W_d\{O''F - (\tan \phi)(O''A)\} \qquad \text{5g}$$

(Solving Eq. 5g for tan $\phi$):

$$\tan \phi = \frac{(W_d)(O''F) - (W_g)(O'E)}{(W_g)(O'A) + (W_d)(O''A)} \qquad \text{Eq. 6}$$

In the specific embodiment where the device mass is 329 grams, the above-defined distances have the following values:

A. With groove 6 serving as the axis of revolution (for the 1000 cc bottle).
(1) O"F = 1.05 inches
(2) O'E = 2.07 inches
(3) O'A = 2.07 inches
(4) O"A = 2.91 inches B. With groove 10 serving as the axis of revolution (for the 500 cc bottle).
(1) O"F = 1.30 inches
(2) O'E = 1.82 inches
(3) O'A = 2.07 inches
(4) O"A = 2.91 inches C. With groove 11 serving as the axis of revolution (for the 250 cc bottle).
(1) O"F = 1.57 inches
(2) O'E = 1.55 inches
(3) O'A = 2.07 inches
(4) O"A = 2.91 inches D. With groove 12 serving as the axis of revolution (for the plastic bag).
(1) O"F = 2.26 inches
(2) O'E = 0.86 inches
(3) O'A = 2.07 inches
(4) O"A = 2.91 inches The above-listed values take into account the differences in mass between the different types of liquid containers. In general, the determination as to where to locate each of the hanger portion grooves can be made as follows. First, a determination is made of the horizontal distance HD between the device center of gravity and the groove 14. (HD is equal to the sum of O'E and O"F.) Second, a decision is made as to the minimum suspended weight ($W_{min}$) desired for the particular type of container to have at the time the alarm signal is to be given. In this connection, it is important that account be taken of container weight tolerances to ensure that when a relatively heavy container is used the alarm can be given when the container is empty. Third, the horizontal spacing O"F can be calculated from the following formula.

$$O''F = \left[ \frac{HD}{1 + (W_{min}/W_g)} \right]$$

An empty plastic bag has a nominal mass of 40 grams, and a tolerance of ±4 grams. An empty 250 cc bottle has a nominal mass of 226 grams, and a tolerance of ±11 grams. An empty 500 cc bottle has a nominal mass of 341 grams, and a tolerance of ±21 grams. An empty 1000 cc bottle has a nominal mass of 530 grams, and a tolerance of ±21 grams. Other weights are involved; these include hanging apparatus, such as the bottle handle, typically having a mass of 25 grams ±3 grams; and tubing plus liquid therein typically having a mass of 40 grams ±5 grams.

A specific numerical example is now presented for the case where a plastic bag is used. When filled, the plastic bag, the liquid therein, and the other weights such as tubing amount to 1080 grams typically. Thus, the initial value for $\phi$ is given as follows:

$$\tan \phi = \frac{(1080 \text{ grams}) (2.26 \text{ inches}) - (329 \text{ grams}) (0.86 \text{ inches})}{(329 \text{ grams}) (2.07 \text{ inches}) + (1080 \text{ grams}) (2.91 \text{ inches})}$$

$\tan \phi = 0.56$
$\phi = 29.4$ degrees

After 500 cc of liquid has been dispensed, the mass will have decreased from the starting value of 1080 grams to an instantaneous value of 580 grams. At this point in time, the value for $\phi$ is given as follows:

$$\tan \phi = \frac{(580 \text{ grams}) (2.26 \text{ inches}) - (329 \text{ grams}) (0.86 \text{ inches})}{(329 \text{ grams}) (2.07 \text{ inches}) + (580 \text{ grams}) (2.91 \text{ inches})}$$

$\tan \phi = 0.43$
$\phi = 23.5$ degrees

The value of $\phi$ will continue to decrease with time as more liquid is dispensed. After approximately 955 cc of liquid has been dispensed, $\phi$ reaches zero degrees. At this point, the mercury switch "makes" and the audible alarm is given.

I claim:

1. An intravenous alarm device for providing an alarm signal to indicate that a predetermined amount of liquid remains in a liquid dispensing container of the type adapted to be suspended from an arm, the intravenous alarm device comprising:

attitude-sensitive transducing means including a mercury switch that defines a reference axis and that has two contacts between which mercury makes electrical connection while the reference axis is within a predetermined tolerance angle relative to horizontal, and including circuit means controlled by the mercury switch for producing such an alarm signal while the mercury makes electrical connection between the contacts;

a structure including a casing and support means for supporting the attitude-sensitive transducing means; the support means including a board for supporting the mercury switch, and adjustable means for presetting the orientation of the board relative to the casing to provide tolerance compensation such that the alarm is produced only while the angle between the reference axis and horizontal is less than the tolerance angle;

the casing having at a first point thereof a hanger portion to provide for suspending the device from such an arm, having at a second point thereof a holding portion from which such a liquid dispensing container can be suspended, and having defined at a third point thereof a device center of gravity;

the hanger portion defining an axis of revolution perpendicular to said reference axis; and the first, second, and third points being spaced relative to each other to define vertices of a triangle such that the structure, while being suspended from such an arm and having suspended from it such a liquid dispensing container that is dispensing liquid, orients the reference axis at a time-varying angle relative to the horizontal with the instantaneous magnitude of the time-varying angle being dependent upon the weight of the liquid remaining in the suspended liquid container.

2. A device according to claim 1 wherein the hanger portion includes a plurality of spaced-apart grooves each for use in defining the axis of revolution in conjunction with a respective one of a plurality of different containers.

3. A device according to claim 1 wherein the structure includes manually adjustable means for adjusting the position of the point at which the device center of gravity is defined.

4. A device according to claim 3 wherein said manually adjustable means includes a track portion of the casing and a counterweight movable to any one of a plurality of selected positions along the track portion.

5. A device according to claim 1 wherein the alarm signal producing means includes gated oscillator circuit means responsive to the mercury switch.

* * * * *